United States Patent [19]
Herrlein

[11] Patent Number: 6,085,579
[45] Date of Patent: Jul. 11, 2000

[54] METHOD FOR ASSESSING DISPOSABLE ABSORBENT STRUCTURES

[75] Inventor: Mathais Kurt Herrlein, Frankfurt, Germany

[73] Assignee: The Procter & Gamble Company, Cincinnati, Ohio

[21] Appl. No.: 09/155,467

[22] PCT Filed: Mar. 25, 1997

[86] PCT No.: PCT/US97/04860

§ 371 Date: Sep. 29, 1998

§ 102(e) Date: Sep. 29, 1998

[87] PCT Pub. No.: WO97/32708

PCT Pub. Date: Oct. 9, 1997

[30] Foreign Application Priority Data

Mar. 29, 1996 [GB] United Kingdom ................. 96105022

[51] Int. Cl.[7] .............................. G01N 5/02; A61F 13/00
[52] U.S. Cl. ................................. 73/73; 73/76; 604/358; 604/378
[58] Field of Search ........................ 73/73, 76; 604/368, 604/378, 358

[56] References Cited

U.S. PATENT DOCUMENTS

| | | | |
|---|---|---|---|
| 3,632,361 | 1/1972 | Battista | 106/122 |
| 4,759,354 | 7/1988 | Quarfoot | 602/50 |
| 4,798,603 | 1/1989 | Meyer et al. | 604/378 |
| 5,147,343 | 9/1992 | Kellenberger | 604/368 |
| 5,509,915 | 4/1996 | Hanson et al. | 604/378 |
| 5,961,506 | 10/1999 | Guidotti et al. | 604/378 |

*Primary Examiner*—Hezron Williams
*Assistant Examiner*—Michael Cygan
*Attorney, Agent, or Firm*—Edward J. Milbrada; Mary Catherine Hentz; Steven W. Miller

[57] ABSTRACT

The invention refers to methods for assessing absorbent structures (10) for their fluid handling ability by using materials (110) having a moisture pick up ability which is very close to the one of human skin. This is achieved by using materials (110) which do not function based on capillary transport for moisture, but which comprise as an essential element swellable but non-soluble materials in a film form. Such materials (110) can be based on proteins, Glycin, Prolin, 4-hydroxyprolin, naturally occurring sugars, glycerin, sorbit and collagen. A particularly preferred material is a film material comprising collagen. To simulate a baby's weight upon the absorbent structure (10), a load (16) may be utilized therewith.

5 Claims, 2 Drawing Sheets

6,085,579

METHOD FOR ASSESSING DISPOSABLE ABSORBENT STRUCTURES

The present invention relates to a method for assessing disposable absorbent structures for their fluid handling ability. More specifically, the present invention relates to materials which are particularly suitable for such an assessment.

BACKGROUND OF THE INVENTION

Disposable, absorbent articles such as diapers, incontinence articles, sanitary towels, training pants and the like are well known in the art.

Significant effort has already been spent against assessing the performance of such articles both with respect to wetting of outer garments (leakage) and with respect to wetting or lack thereof of the skin of the wearer.

To assess the condition of the skin of the wearer, the moisture content of the uppermost skin layer, the stratum corneo, is of critical importance, and many reports refer to the evaluation of such articles under in-vivo conditions.

Elsner et al. provides a comprehensive overview of such methods in "Bioengineering of the skin: Water and the Stratum Corneum", CRC Press, 1994. The most relevant methods are the "Transepidermal Water Loss" (often abbreviated TEWL) measuring the moisture evaporation from the skin; methods to measure the electrical properties like capacitance, impedance, or conductance of the skin, which depend strongly on the moisture content, such as with the CORNEOMETER or NOVA or other instruments. Also, further methods applying conventional chemical analysis tools like IR or NMR spectroscopic or magnetic resonance imaging are referred, too, however, have so far not found broad application.

The in-vivo methods have in common, that they asses directly the condition of the skin of the wearer of an absorbent article either under real in-use loadings or possibly with artificially loaded articles, which are for example worn on the forearm of a test person for a certain period.

For all these methods, the comparison of absorbent articles for development purposes is cumbersome. Apart from the fact of needing test persons as such, these persons have individual factors—such as varying reaction to certain room conditions as temperature or relative humidity—all contributing to a large variability of the test results. In order to still get meaningful data, the number of test persons must be increased—again increasing the effort.

Hence, significant effort has already been put against evaluating absorbent articles and structures under reproducible and easy to execute laboratory conditions, whereby generally the human skin is replaced by standardised fluid pick-up filter paper. Essentially, these methods are based on the "capillary rewet" principle, whereby a test sample is loaded with a certain amount of test fluid, such as synthetic urine. After a certain time such as to allow for equilibration and preferably under a certain pressure, the pick up filter paper as "skin replacement" is placed on top of the surface of the loaded structure for a certain time, under a certain pressure. The pick-up filter paper is well defined such as by porosity, basis weight, or absorbency. Due to the capillary suction power of its pores, it is sucking up readily available moisture (i.e. "free" moisture not being bound such as through superabsorbent materials or in smaller pores that the pick-up paper) from the surface of the test specimen and the weight increase is a measure for the "rewet" performance of the absorbent article.

Optionally, this test procedure can be combined with other fluid handling evaluation protocols, for example a "post-acquisition-rewet-test" indicates, that during the first part of the combine protocol the fluid acquisition behaviour of the test specimen is studied, whereas the rewet assessment in then carried out in the second part of the test.

A big number of such tests have been described in the public, such as in WO 93/02 188 (Guidotti et al.); EP-A-0 039 974 (Mullane); EP-A-0 278 601 (Kobayashi); or EP-A-0 539 703 (Hanson).

Another approach to assess the performance of such articles has been proposed by Lask et al. in EP-B-0 312 919, whereby the surface moisture e.g. of an absorbent article is correlated to the reflection and scattering of a light beam.

However, advanced core designs have resulted in "dryer and dryer" products, and the differentiation between "good" and "better" products has become increasingly difficult, if not impossible with these conventional methods. Still, both in-vivo measurements as well as comments of users of such articles clearly indicate, that there is a need for further discerning various products or designs to further improve the performance of such articles, and in particular to reduce skin hydration.

In addition, recent work indicated, that it not only the capillary fluid transport from the loaded article back to the skin of the wearer is impacting on the condition of the skin, but that other factors such as sweating under occlusive conditions can have very negative impact on the condition of the skin.

Hence it is been an object of the invention to provide a better tool for distinguishing well performing absorbent articles under reproducible laboratory conditions.

It is a further object of the invention to provide such a tool not only for capillary fluid transfer conditions, but also for other moisture transfer mechanisms, such as when sweating under occlusive conditions.

Thus the invention provides particularly well suited materials, which—when combined with the appropriate test protocol—allow significantly improved differentiation of absorbent articles.

SUMMARY OF THE INVENTION

The invention relates to a method for assessing absorbent structures using materials having a moisture pick up ability which is very close to the behaviour of human skin. This is achieved by using materials which do not function based on capillary transport for moisture, but which comprise as an essential element swellable but insoluble materials, preferably in film form. Such materials can be based on proteins, Glycin, Prolin, 4-hydroxyprolin, naturally occurring sugars, glycerin, sorbit, collagen. A particularly preferred material is a film material comprising collagen, as known in the medical art for wound coverages or for food packaging. Such materials allow very effective distinction of absorbent articles, in particular when used in a test protocol optimised for both the "pick-up" material as well as for the absorbent structure under evaluation.

The method of the invention provides benefits versus in-vivo experiments in allowing standardised testing condition, thus allowing much speedier. It provides benefits over porous rewet test materials for conventional testing protocols, as it is not using the unrealistic capillary liquid transport from the pores of the absorbent article to the pores of the "rewet pick-up" material, generally a specific type of filter paper.

DETAILED DESCRIPTION

Figure 1:
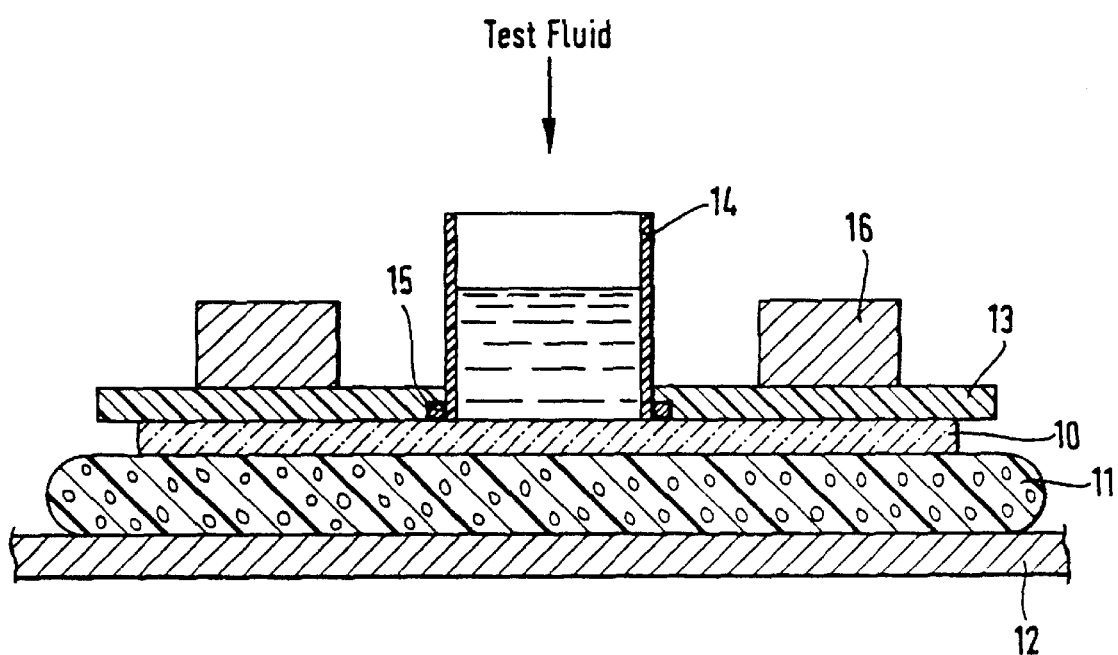
FIG. 1 shows a simplified test equipment according to a preferred test protocol for assessing skin hydration performance of baby diapers.

The invention relates to materials suitable for a novel way of assessing the impact of absorbent articles on the hydration condition of human skin. It aims at providing such materials for reliable laboratory tests without negative effects of in-vivo experiments on one side, and laboratory tests focusing on capillary liquid transfer or free surface moisture on the other side.

The key element of the materials according to the current invention is the lack of a porous structure whilst the materials have the ability to pick up moisture by a similar mechanism as human skin. This is achieved by using "hydratable" materials, which on one side have the ability to pick up moisture, which, however, on the other side do maintain their generally film like structure even at equilibrium saturation, and do not disintegrate or wet upon wetting. Therby, the moisture pick up is dominated by hydration mechanisms, i.e. in contrast to the mechanisms of porous and/or fibrous structures, the fluid is transferred to the pick-up materials according to the present invention not by capillary transport through said pores, but rather by directly diffusing into the molecular matrix of the pick up materials, and by hydrogen bonding mechanisms dominating the moisture adsorption in these materials.

This mechanism should also be seen in contrast to the swelling of—for example—cellulosic fibre structures. Whilst the cellulosic fibres do exhibit a certain swelling, and also exhibit a certain ability to bind liquid through hydrogen bonding within the fibres, the dominating mechanism is the liquid retention in the interstitial voids, i.e. the interfibre pores. In contrast, even if materials according to the presnet invention would be applied in a fibrous form, it is an essential element, that the dominating absorption of fluid is not into the pores of such a structure comprising fibres and fibre interstitials, but into the the fibres itself.

Materials exhibiting the fluid pick up ability are proteins in general, prolin, 4-hydroxyprolin, natural sugars, glycerine, sorbit, but a particularly preferred material is collagen.

Collagens are generally natural based materials, which are produced by starting from bovine skin skives. Preferred materials are partly modified insoluble collagen films. Making of such films for use in medical applications such as wound coverings is disclosed in WO 94/04201 assigned to NATURIN GmbH, Germany, who is also a supplier of such materials. Other applications of collagen containing films is in the food industry for use as edible sausage of ham casings.

Preferred execution of these films is "Collagen Food Film" manufactured and sold by NATURIN under the designation "COFFI". Such embossed films have a basis weight of about 28 g/m2. The materials have a closely monitored moisture content of about 12% by weight. With this moisture, the film material is flexible and easy to handle. Upon further drying, it starts to become brittle. If in contact with moisture—be this in the form of liquid or vapour—the material starts to further soften and swells up to an equilibrium moisture of 150% of its initial weight.

It has been found, that this material is an excellent replica for simulating moisture pick up behaviour of human skin, if applied in an appropriate test protocol.

Obviously, this protocol needs to be adjusted according to the object under evaluation, i.e. the protocol for a baby diaper should be different for a test protocol for an Adult Incontinence product, or a catamenial device.

In all these cases, the conditions should be varied such is that the collagen material should be allowed be to increase its own weight to about 50% of the equilibrium moisture content under realistic loading conditions of the respective article. It will be straightforward for the man skilled in the art to adjust any of the test parameter as laid out in the following example.

Test Procedures

The following exemplifies the procedure to evaluate baby diapers, and more specifically baby diapers of the broadly distributed MAXIIMAXI PLUS size (i.e infants in the weight range from about 8 kg to about 18 kg).

General

All tests are carried out at about 22+/−2° C. and at 35+/−15% relative humidity. The synthetic urine used in the test methods is commonly known as Jayco SynUrine and is available from Jayco Pharmaceuticals Company of Camp Hill, Pa. The formula for the synthetic urine is: 2.0 g/: of KCl; 2.0 g/l of Na2SO4, 0.85 g/l of (NH4)H2PO4; 0.15 g/l (NH4)H2PO4; 0.19 g/l of CaCl2; ad 0.23 g/l of MgCl2. All of the chemicals are of reagent grade. The pH of the synthetic Urine is in the range of 6.0 to 6.4.

Acquisition Test

Referring to FIG. 1, an absorbent structure (10) is loaded with a 75 ml gush of synthetic urine at a rate of 15 ml/s using a pump (Model 7520-00, supplied by Cole Parmer Instruments., Chicago, U.S.A.), from a height of 5 cm above the sample surface. The time to absorb the urine is recorded by a timer. The gush is repeated every 5 minutes at precisely 5 minute gush intervals until the article is sufficiently loaded. Current test data are generated by loading four times.

The test sample, which comprises a core and includes a topsheet and a backsheet, is arranged to lie flat on a foam platform 11 within a perspex box (only base 12 of which is shown). A perspex plate 13 having a 5 cm diameter opening substantially in its middle is placed on top of the sample. Synthetic urine is introduced to the sample through a cylinder 14 fitted, and glued into the opening. Electrodes 15 are located on the lowest surface of the plate, in contact with the surface of the absorbent structure 10. The electrodes are connected to the timer. Loads 16 are placed on top of the plate to simulate, for example a baby's weight. A pressure of 50 g cm-2 (0.7 psi) is typically utilised in this test.

As test fluid is introduced into the cylinder it typically builds up on top of the absorbent structure thereby completing an electrical circuit between the electrodes. This starts the timer. The timer is stopped when the absorbent structure has absorbed the gush of urine, and the electrical contact between the electrodes is broken.

The acquisition rate is defined as the gush volume absorbed (ml) per unit time (s). The acquisition rate is calculated for each gush introduced into the sample. Of particular interest in view of the current invention are the first and the last of the four gushes.

This test is primarily designed to evaluate products having an absorbent capacity of about 300 ml to 400 ml. If products with significantly different capacities should be evaluated, the settings in particular of the fluid volume per gush should be adjusted appropriately to about 20% of the theoretical capacity, and the deviations should be recorded.

Figure 2:
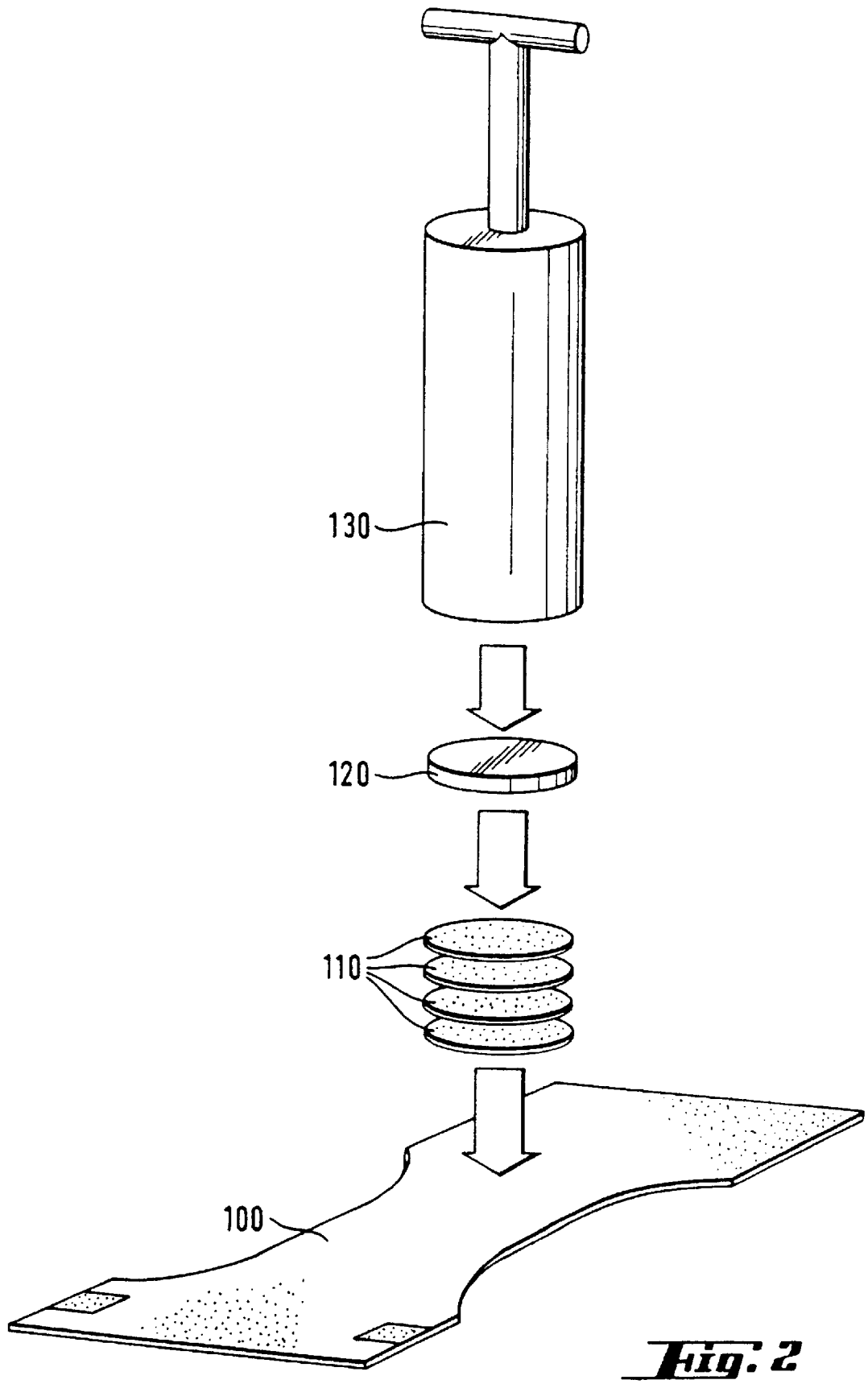
FIG. 2 shows a simplified test equipment for assessing the liquid acquisition performance of baby diapers.

Skin Hydration Value determination (refer to FIG. 2)

Before executing the test, the collagen film as purchased from NATURIN GmbH, Weinhein, Germany, is prepared by being cut into sheets of 90 mm diameter by using a sample cutter device and by equilibrating the film in the controlled environment of the test room (see above) for at least 12 hrs (tweezers are to be used for all handling of the collagen film).

At least 5 minutes, but not more than 6 minutes after the last gush of the above acquisition test is absorbed, the cover plate and weights are removed, and the test sample (100) is carefully placed flat on a lab bench.

4 sheets of the precut and equilibrated collagen material (110) are weighed with at least one milligram accuracy, and then positioned centred onto the loading point of the article, and covered by perspex plate (120) of 90 mm diameter, and about 20 mm thickness. A weight (130) of 15 kg is carefully added (also centred). After 30+/−2 seconds the weight and perspex plate are carefully removed again, and the collagen films are reweighed.

The Skin Hydration Value is the moisture pick up of the collagen film, expressed in g.

Comparative capillary rewet test

A comparative test is executed according the following procedure.

This test is also carried out 10 minutes (+/−5 sec) after the acquisition test, but uses 10 sheets of blotting paper of 220 g/m2 as supplied by Hollinsworth & Vose, UK under the designation of MEDIUM WHITE W/S, and cut to 20 by 10 cm. This is equilibrated and preweighed, and positioned centred onto the loading point. A circular weight of 4860 g (in total) with a perspex plate of 18 cm by 6 cm is covered with a soft foam of a basis weight of 500 g/m2 of 1 cm thickness and a Polyethylene film is carefully positioned onto the filter paper and left on it for 15 seconds.

The value for rewetting is the weight increase of the blotting papers.

Post use evaluation of diapers

Diapers have been give to users for overnight usage on babies. In the morning, the diapers were removed under supervision of an expert grader, who executed NOVAMETER tests according to the NOVAMETER using instructions in the genital region of the babies.

Also, the parents were asked to grade the skin dryness in the genital area on a 4 point scale.

Evaluation of Sample Diapers

In order to further exemplify the benefits of the current invention, samples of different baby diapers have been submitted various test protocols as outlined in the above.

Sample 1 is a commercially available product, PAMPERS Baby Dry Maxi/MAXI PLUS size as marketed by Procter & Gamble in Europe.

Sample 2 is a commercially available product, HUGGIES FLEXIFIT as marketed by Kimberly-Clark in Europe Sample 3 is identical to sample 1 except for the following First, chemically treated stiffened cellulosic material (CS) supplied by Weyerhaeuser Co.,US under the trade designation of "CMC" functioning as an acquisition/distribution layer is doubled in basis weight, by an increase from about 295 g/m2 to 590 g/m2.

Second, an additional acquisition layer in introduced between the topsheet and said chemically treated stiffened cellulose layer, namely a high-loft chemically bonded nonwoven as supplied by FIBERTECH, North America under the designation type 6852. It is a chemically bonded PET fibre web of a basis weight of 42 g/m2.

Thirdly, the cellulose material usage in the storage core underneath the chemically treated stiffened cellulosic material is increased from about 20 g to 40 g per pad.

Fourth, the amount of superabsorbent material in this storage core is increased from about 10 g to about 33 g per pad. Superabsorbent material was supplied by Stockhausen GmbH, Germany under the trade name FAVOR SXM.

The results were as follows:

TABLE 1

|  | Sample 1 | Sample 2 | Sample 3 |
| --- | --- | --- | --- |
| Collagen testing | | | |
| Loading zone rewet [µg] | 152 | 50 | 146 |
| Filter paper rewet [g] | 0.4 | 0.35 | 0.43 |
| Overnight wear study NOVAMETER testing | | | |
| number of babies tested genital area, [−] | 43 540 | 21 366 | 20 548 |
| Mothers skin rating [%] | | | |
| number of babies tested | 21 | 21 | 20 |
| dry | 61 | 63 | 55 |
| slightly damp | 29 | 37 | 30 |
| damp | 10 | 0 | 15 |
| wet | 0 | 0 | 0 |

As can be seen from these test, the at best directional differences in conventional testing between the sample 1 and 3 could be made significant on a statistical basis by applying the present invention. The significant improvement of the sample 2 in on-baby testing is well reflected in the results of the present invention, but not in the conventional testing method.

What is claimed is:

1. A method for assessing disposable absorbent structures for their fluid handling ability whereby the performance of the absorbent structure is assessed by the amount of fluid this structure releases to a pick up material after the structure has been loaded with a test liquid, said method comprising the steps of:

a) providing said absorbent structure;

b) loading said absorbent structure with said test liquid;

c) providing said pick up material and preweighing said pick up material to determine an initial weight;

d) positioning said pick up material on said absorbent structure for a predetermined time under a predetermined pressure such that said absorbent structure releases a portion of said test liquid to said pick up material to load said pick up material;

e) removing said loaded pickup material from said absorbent structure;

f) weighing said loaded pick up material to determine a loaded weight: and g) calculating a Skin Hydration Value by subtracting said initial weight from said loaded weight wherein said pick up material consists essentially of material swellable and insoluble in water; and in that the fluid transfer to the moisture pick up material is dominated by hydration mechanisms.

2. A method according to claim 1, wherein said swellable and insoluble pick up material is selected from proteins, Glycin, Prolin, 4-hydroxyprolin, naturally occurring sugars, glycerin, sorbit and collagen.

3. A method according to claim 2, wherein said pick up material is collagen.

4. A method according to claims 1–3, wherein the moisture pick up material is in film form.

5. A method according to claim 1, wherein said predetermined time is at least 20 seconds and said predetermined pressure is at least 34.5 g/cm2 (0.5 psi).

* * * * *

UNITED STATES PATENT AND TRADEMARK OFFICE
CERTIFICATE OF CORRECTION

PATENT NO.   : 6,085,579
DATED        : July 11, 2000
INVENTOR(S)  : Mathias Kurt Herrlein It is certified that error appears in the above-identified patent and that said Letters Patent is hereby corrected as shown below:

<u>Title page,</u>
Item [75], Inventor: please delete "Mathais" and insert therefor -- Mathias --.

<u>Column 4,</u>
Line 11, please delete "MAXIIMAXI" and insert therefor -- MAXI/MAXI --.
Line 19, after "Na2SO4", please delete "," (the comma) and insert therefor -- ; -- (a semi-colon).

<u>Column 6,</u>
Line 30, after "ability", please insert -- , -- (a comma).
Line 48, after "weight", please delete ":" (the colon) and insert therefor -- ; -- (a semi-colon).

Signed and Sealed this

Fourth Day of February, 2003

JAMES E. ROGAN
*Director of the United States Patent and Trademark Office*